(12) United States Patent
DuBridge et al.

(10) Patent No.: US 6,175,002 B1
(45) Date of Patent: Jan. 16, 2001

(54) ADAPTOR-BASED SEQUENCE ANALYSIS

(75) Inventors: Robert B. DuBridge, Belmont; Glenn Albrecht, Redwood City, both of CA (US); Sydney Brenner, Cambridge (GB); Sergei M. Gryaznov; Sarah N. McCurdy, both of San Mateo, CA (US)

(73) Assignee: Lynx Therapeutics, Inc., Hayward, CA (US)

( * ) Notice: Under 35 U.S.C. 154(b), the term of this patent shall be extended for 0 days.

(21) Appl. No.: 09/225,652

(22) Filed: Jan. 5, 1999

Related U.S. Application Data

(62) Division of application No. 08/842,608, filed on Apr. 15, 1997, now Pat. No. 5,888,737.

(51) Int. Cl.⁷ .......................... C07H 21/00; C07H 21/04
(52) U.S. Cl. ........................... 536/23.1; 536/24.2
(58) Field of Search ................ 435/6; 536/24.2, 536/25.3, 23.1

(56) References Cited

U.S. PATENT DOCUMENTS

| | | |
|---|---|---|
| 5,093,245 | 3/1992 | Keith et al. . |
| 5,270,185 * | 12/1993 | Margolskee ................. 435/91.41 |
| 5,478,893 | 12/1995 | Ghosh et al. . |
| 5,503,980 | 4/1996 | Cantor . |
| 5,508,169 | 4/1996 | Deugau et al. . |
| 5,552,278 | 9/1996 | Brenner ............................. 435/6 |
| 5,599,675 | 2/1997 | Brenner ............................. 436/6 |
| 5,849,544 * | 12/1998 | Harris et al. .................... 435/91.2 |

FOREIGN PATENT DOCUMENTS

| | | |
|---|---|---|
| WO 92/20697 | 11/1992 | (WO) . |
| WO 94/01582 | 1/1994 | (WO) . |
| WO 95/20053 | 7/1995 | (WO) . |
| WO 95/27080 | 10/1995 | (WO) . |

OTHER PUBLICATIONS

Broude, N.E. et al., "Enhanced DNA Sequencing by Hybridization," *Proc. Natl. Acad. Sci. USA*. 91: 3072–3076 (1994).

Bunemann, H. et al., "Immobilization of Denatured DNA to Macroporous Supports: I. Efficency of Different Coupling Procedures," *Nucleic Acids Research*. 10: (22) 7163–7180 (1982).

Ghosh, S.S. and Musso, G.F., "Covalent Attachment of Oligonucleotides to Solid Supports," *Nucleic Acids Research*. 15: (13) 5353–5372 (1987).

Jones, D.H., "An Iterative and Regenerative Method for DNA Sequencing," *BioTechniques*. 32: (05) 938–946 (1997).

Kremsky, J.N. et al., "Immobilization of DNA via Oligonucleotides Containing an Aldehyde or Carboxylic Acid Goup at the 5' Terminus," *Nucleic Acids Research*. 15 (07) 2891–2909 (1987).

Kuznetsova, S.A. et al., "DNA Sequencing by Hybridization with Gel–Immobilized Oligonucleotides: Expanding Applicability with Chemical Ligation," *Molecular Biology*. 28: (02) 190–195 (1994).

Wolf, S.F. et al., "Rapid Hybridization Kinetics of DNA Attached to Submicron Latex Particles," *Nucleic Acids Research*. 15: (07) 2911–2926 (1987).

* cited by examiner

*Primary Examiner*—Robert A. Schwartzman
*Assistant Examiner*—Thomas G. Larson
(74) *Attorney, Agent, or Firm*—Stephen C. Macevicz; Vincent M. Powers; LeeAnn Gorthey

(57) ABSTRACT

An improvement in adaptor-based sequence analysis is provided that addresses the problems created by self-ligation of target polynucleotides that have complementary ends. The improvement includes preparation of target polynucleotides with dephosphorylated 5' strands and the use of adaptors having a 3' blocking group. In a preferred embodiment, adaptors are ligated to target polynucleotides by a single strand, 3' blocking groups are removed, the adjacent 5' hydroxyl of the target polynucleotide is phosphorylated, and the ligation of the adaptor is completed by treatment with a ligase.

8 Claims, 8 Drawing Sheets

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
    (A) LENGTH: 28 nucleotides
    (B) TYPE: nucleic acid
    (C) STRANDEDNESS: double
    (D) TOPOLOGY: linear (xi) SEQUENCE DESCRIPTION: SEQ ID NO: 1:

TGGATTCTAG AGAGAGAGAG AGAGAGAG                                28

(2) INFORMATION FOR SEQ ID NO: 2:

(i) SEQUENCE CHARACTERISTICS:
        (A) LENGTH: 16 nucleotides
        (B) TYPE: nucleic acid
        (C) STRANDEDNESS: double
        (D) TOPOLOGY: linear (xi) SEQUENCE DESCRIPTION: SEQ ID NO: 2:

NNGGATGNNN NNNNNN                                             16

(2) INFORMATION FOR SEQ ID NO: 3:

(i) SEQUENCE CHARACTERISTICS:
        (A) LENGTH: 15 nucleotides
        (B) TYPE: nucleic acid
        (C) STRANDEDNESS: double
        (D) TOPOLOGY: linear (xi) SEQUENCE DESCRIPTION: SEQ ID NO: 3:

NNGGATGNGA TATCN                                              15

(2) INFORMATION FOR SEQ ID NO: 4:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (xi) SEQUENCE DESCRIPTION: SEQ ID NO: 4:

CTAAACCATT GGTATGGGCC AGTGAATTGT AATA                         34

(2) INFORMATION FOR SEQ ID NO: 5:

(i) SEQUENCE CHARACTERISTICS:
        (A) LENGTH: 55 nucleotides
        (B) TYPE: nucleic acid
        (C) STRANDEDNESS: single
        (D) TOPOLOGY: linear (xi) SEQUENCE DESCRIPTION: SEQ ID NO: 5:

CGCGCAGCCC GCATCGTTTA TGCTACAGAC TGTCAGTGCA                   40

GCTCTCCGAT CCAAA                                              55

(2) INFORMATION FOR SEQ ID NO: 6:

(i) SEQUENCE CHARACTERISTICS:
        (A) LENGTH: 24 nucleotides
        (B) TYPE: nucleic acid
        (C) STRANDEDNESS: double
        (D) TOPOLOGY: linear (xi) SEQUENCE DESCRIPTION: SEQ ID NO: 6:

GNNNTACGTG CGCATCCCGA GCNA                                    24

```
(2) INFORMATION FOR SEQ ID NO: 7:

(i) SEQUENCE CHARACTERISTICS:
        (A) LENGTH: 24 nucleotides
        (B) TYPE: nucleic acid
        (C) STRANDEDNESS:  double
        (D) TOPOLOGY:  linear (xi) SEQUENCE DESCRIPTION: SEQ ID NO: 7:

TNNNTACGTG CGCATCCCGA GCNA                                          24

(2) INFORMATION FOR SEQ ID NO: 8:

(i) SEQUENCE CHARACTERISTICS:
        (A) LENGTH: 24 nucleotides
        (B) TYPE: nucleic acid
        (C) STRANDEDNESS:  double
        (D) TOPOLOGY:  linear (xi) SEQUENCE DESCRIPTION: SEQ ID NO: 8:

CNNNTACGTG CGCATCCCGA GCNA                                          24

(2) INFORMATION FOR SEQ ID NO: 9:

(i) SEQUENCE CHARACTERISTICS:
        (A) LENGTH: 24 nucleotides
        (B) TYPE: nucleic acid
        (C) STRANDEDNESS:  double
        (D) TOPOLOGY:  linear (xi) SEQUENCE DESCRIPTION: SEQ ID NO: 9:

ANNNTACGTG CGCATCCCGA GCNA                                          24
```

ADAPTOR-BASED SEQUENCE ANALYSIS

This is a Division of application. Ser. No. 08/842,608 filed Apr. 15, 1997, now U.S. Pat. No. 5,888,737, which is hereby incorporated by reference.

FIELD OF THE INVENTION

The invention relates generally to improved methods and compositions for analyzing nucleic acids, and more particularly, to a method of analyzing terminal nucleotides of polynucleotides by specific ligation of labeled adaptors.

BACKGROUND

The desire to understand the genetic basis of disease and a host of other physiological states associated different patterns of gene expression has led to the development of several approaches to large-scale analysis of DNA, Adams et al, Editors, Adams DNA Sequencing and Analysis (Academic Press, New York, 1994). Current techniques for analyzing gene expression patterns include large-scale sequencing, differential display, indexing schemes, subtraction hybridization, hybridization with solid phase arrays of cDNAs or oligonucleotides, and numerous DNA fingerprinting techniques, e.g. Lingo et al, Science, 257: 967–971 (1992); Erlander et al, International patent application PCT/US94/13041; McClelland et al, U.S. Pat. No. 5,437,975; Unrau et al. Gene, 145: 163–169 (1994); Schena et al, Science, 270: 467–469 (1995); Velculescu et al. Science, 270: 484–486 (1995); and the like.

An important subclass of such techniques employs double stranded oligonucleotide adaptors to classify populations of polynucleotides and/or to identify nucleotides at the termini of polynucleotides, e.g. Unrau et al (cited above) and U.S. Pat. No. 5,508,169; Sibson, International applications PCT/GB93/01452 and PCT/GB95/00109; Cantor, U.S. Pat. No. 5,503,980; and Brerner, International application PCT/US95/03678 and U.S. Pat. No. 5,552,278. Such adaptors typically have protruding strands which permit specific hybridization and ligation to polynucleotides having complementary ends. Identification or classification is effected by carrying out such reactions in separate vessels or by providing labels which identify one or more nucleotides in the protruding strand of the ligated adaptor.

In these techniques, special problems arise in dealing with either polynucleotide ends or adaptors that are capable of self-ligation, such as that illustrated in FIG. 1, where the four-nucleotide protruding strands of the anchored polynucleotides are complementary to one another. When self-ligation occurs, the protruding strands of either the adaptors or the target polynucleotides are no longer available for analysis or processing. This, in turn, leads to the loss or disappearance of signals generated in response to correct ligations of adaptors to target polynucleotides. The self-ligation problem is especially acute when identical target polynucleotides are anchored to a solid phase support. In this situation, the local concentration of ends capable of self-ligation is typically very high relative to that of double stranded adaptors, thereby making self-ligation the favored reaction, whenever complementary sequences are present. As illustrated in FIG. 1, complementary sequences form a palindromic duplex upon hybridization. Since the probability of a palindromic 4-mer occurring in a random sequence is the same as the probability of a repeated pair of nucleotides (6.25%), adaptor-based methods for de novo sequencing have a high expectation of failure after a few cycles because of self-ligation. When this occurs, further analysis of the polynucleotide becomes impossible.

In view of the increasing importance of adaptor-based techniques in nucleic acid sequence analysis, the availability of methods and materials for overcoming the self-ligation problem would be highly desirable.

SUMMARY OF THE INVENTION

Accordingly, an object of our invention is to provide an adaptor-based analysis method in which neither the adaptors nor target polynucleotides self-ligate.

Another object of our invention is to provide an improved method of DNA sequencing by ligation wherein identical target polynucleotides anchored to a solid phase support cannot ligate to one another in the presence of a ligase.

A further object of our invention is to provide oligonucleotide adaptors which cannot ligate to one another, but at the same time are capable of being ligated to a target polynucleotide having a complementary protruding strand.

Another object of our invention is to provide compositions comprising uniform populations of identical polynucleotides anchored by one end to a solid phase support, the polynucleotides having at their free ends a protruding strand lacking a 5' phosphate group.

The invention achieves these and other objectives by providing methods and compositions for analyzing polynucleotides using double stranded adaptors. An important aspect of the invention is the removal of the 5' phosphate from the end of the polynucleotide to be analyzed so that self-ligation cannot occur, particularly in embodiments employing enzymatic ligation. Another important aspect of the invention is the use of double stranded adaptors each having a protruding strand complementary to that of the polynucleotides to be analyzed and each having a strand with a blocked 3' carbon so that the strand cannot be ligated. Preferably, double stranded adaptors of the invention are defined by the formulas:

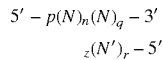

or

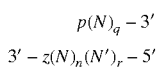

where N is a nucleotide and N' is its complement, p is a phosphate group, z is a 3' blocking group, n is an integer between 2 and 6, inclusive, q is an integer greater than or equal to 8, and r is an integer greater than or equal to 8, which may be the same or different from q.

Preferably, z is a phosphate group and the double stranded portion of the adaptors contain a nuclease recognition site of a nuclease whose recognition site is separate from its cleavage site. As described more fully below, the latter element is useful in embodiments employing repeated cycles of ligation and cleavage for DNA sequencing.

In a preferred embodiment, illustrated in FIG. 2a, the invention provides a method for determining the identity of nucleotides at the terminus of a polynucleotide. The method comprises the following steps: (a) ligating a double stranded adaptor to an end of the polynucleotide, the end of the polynucleotide having a dephosphorylated 5' hydroxyl and the double stranded adaptor having a first strand and a second strand, the second strand of the double stranded adaptor having a 3' blocking group; (b) removing the 3' blocking group after ligation of the first strand; (c) phosphorylating the 5' hydroxyl of the polynucleotide; (d) ligating a second strand having an unblocked 3' moiety to regenerate the double stranded adaptor; and (e) identifying one or more nucleotides at the end of the polynucleotide by the identity of the adaptor ligated thereto. The step of removing the 3' blocking group may be carried out in several ways, including physically removing, e.g. by washing, the entire 3' blocked second strand followed by replacement with an unblocked strand, by chemically or enzyrmatically removing the 3' blocking group, or by otherwise activating or regenerating a 3' hydroxyl on the second strand without removal of the second strand. A 3' phosphate is the preferred 3' blocking group and the step of removing is preferably carried out by treating the second strand with a phosphatase to remove the 3' phosphate and to regenerate a free 3' hydroxyl.

In further preference, the double stranded adaptor includes a recognition site of a nuclease whose recognition site is separate from its cleavage site. This permits one to carry out repeated cycles of ligation and cleavage to identify additional nucleotides of the target polynucleotide. Accordingly, the method of the invention preferably includes the further steps of (f) cleaving said polynucleotide with a nuclease recognizing said nuclease recognition site of said double stranded adaptor such that said polynucleotide is shortened by one or more nucleotides, (g) treating said cleaved polynucleotide to remove a 5' terminal phosphate group whenever said step of cleaving results in the formation of such 5' terminal phosphate group, and (h) repeating said steps (a) through (g) until said nucleotide sequence of the polynucleotide is determined.

In another important embodiment, the invention provides a method for classifying polynucleotides of a population by the use of double stranded adaptors. Generally, in this aspect of the invention polynucleotides are classified by (a) treating the polynucleotides of the mixture with an endonuclease to produce polynucleotides with protruding strands. (b) ligating a double stranded adaptor to a polynucleotide in the mixture, the polynucleotide having a complementary protruding strand to that of the double stranded adaptor, the end of the polynucleotide having a dephosphorylated 5' hydroxyl, and the double stranded adaptor having a first strand and a second strand, wherein the second strand of the double stranded adaptor has a 3' blocking group, (c) removing the 3' blocking group after ligation of the first strand, (d) phosphorylating the 5' hydroxyl of the polynucleotide, (e) ligating a second strand having an unblocked 3' moiety to regenerate the double stranded adaptor; and (f) classifying the polynucleotide by the identity of the adaptor ligated thereto.

The present invention overcomes key problems in adaptor-based methods for analyzing or sequencing DNA: Namely, the problems of self-ligation of target polynucleotides and adaptors. Without self-ligation, adaptor-based methods are rendered significantly more efficient and reliable which, in turn, greatly enhances their commercial applicability.

DEFINITIONS

Figure 1:
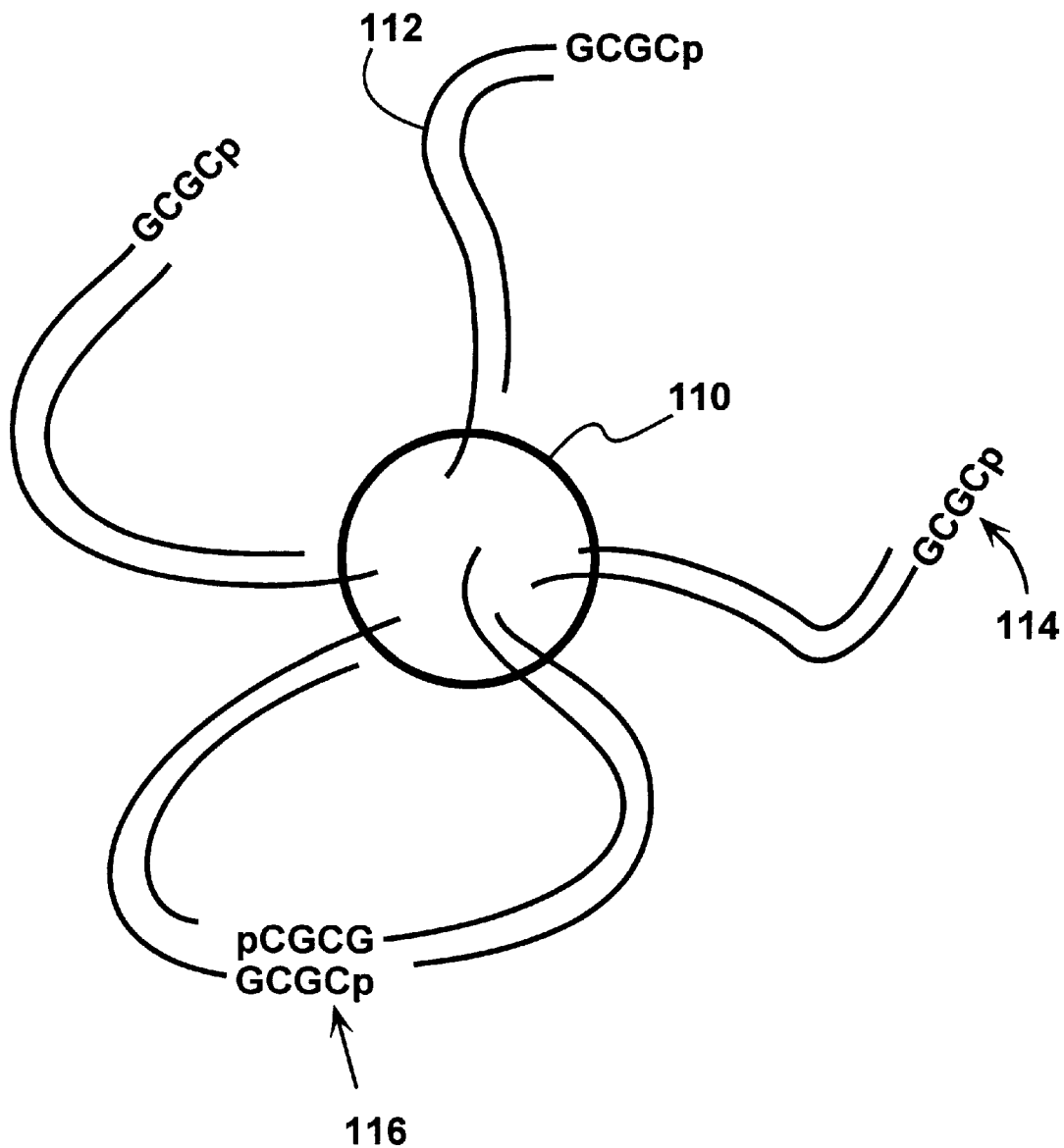
FIG. 1 illustrates the phenomena of self-ligation of identical polynucleotides that are anchored to a solid phase support.

As used herein, the term "ligation" means the formation of a covalent bond between the ends of one or more (usually two) oligonucleotides. The term usually refers to the formation of a phosphodiester bond resulting from the following reaction, which is usually catalyzed by a ligase:

$oligo_1(5')$—OP(O—)(=O)O+HO—$(3')oligo_2$-5'→$oligo_1$(5')—OP(O—)(=O)O—$(3')oligo_2$-5' where $oligo_1$ and $oligo_2$ are either two different oligonucleotides or different ends of the same oligonucleotide. The term encompasses non-enzymatic formation of phosphodiester bonds, as well as the formation of non-phosphodiester covalent bonds between the ends of oligonucleotides, such as phosphorothioate bonds, disulfide bonds, and the like.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence identification may be effected by identifying the ordering and locations of a single type of nucleotide, e.g. cytosines, within a target polynucleotide so that its sequence is represented as a binary code, e.g. "100101 . . . " for "C-(not C)-(not C)-C-(not C)-C . . . " and the like.

"Perfectly matched duplex" in reference to the protruding strands of probes and target polynucleotides means that the protruding strand from one forms a double stranded structure with the other such that each nucleotide in the double stranded structure undergoes Watson-Crick base pairing with a nucleotide on the opposite strand. The term also comprehends the pairing of nucleoside analogs, such as deoxyinosine, nucleosides with 2-aminopurine bases, and the like, that may be employed to reduce the complexity of the adaptors.

The term "oligonucleotide" as used herein includes linear oligomers of nucleosides or analogs thereof, including deoxyribonucleosides, ribonucleosides, and the like. Usually oligonucleotides range in size from a few monomeric units, e.g. 3–4, to several hundreds of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, reduce degeneracy, increase specificity, and the like.

DETAILED DESCRIPTION OF THE INVENTION

Methods and compositions of the invention find application in a multitude of nucleic analysis techniques employing double stranded oligonucleotide adaptors which are ligated to polynucleotides for analysis, particularly indexing schemes (Unrau et al (cited above) and Sibson (cited above)), and DNA sequencing schemes (Cantor (cited above), Brenner (cited above), and Sibson (cited above)).

As illustrated in FIG. 1, an important feature of the invention was the discovery that adaptor-based analysis methods can break down completely when "self-complementary" sequences (114) are present in free protruding strands. This problem is especially severe in embodiments where the polynucleotides (112) to be analyzed are presented to the adaptors as uniform populations of identical polynucleotides attached to a solid phase support (110). In these situations, the free ends of the anchored polynucleotides can twist around to form perfectly matched duplexes (116) with one another. If the 5' strands of the ends are phosphorylated, the polynucleotides are readily ligated in the presence of a ligase. An analogous problem also exists for double stranded adaptors. Namely, whenever their 5' strands are phosphorylated, the 5' strand of one adaptor may be ligated to the free 3' hydroxyl of another adaptor whenever the nucleotide sequences of their protruding strands are complementary.

Figure 2A:
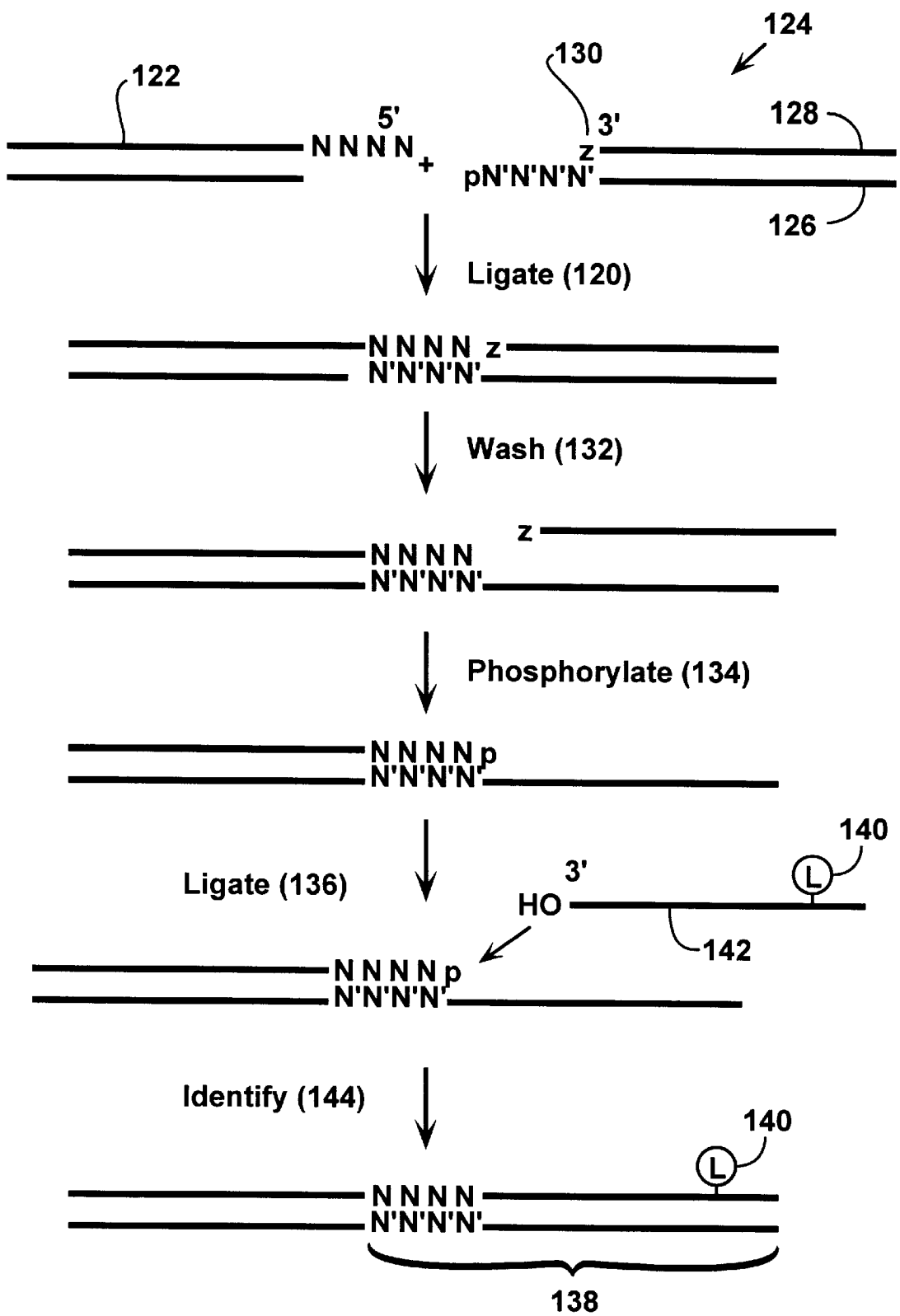
FIG. 2a illustrates steps in a preferred method of the invention in which a double stranded adaptor having a blocked 3' carbon is ligated to a target polynucleotide.

Generally, the method of the invention addresses the above problems by the following steps, which are illustrated in FIG. 2a for a preferred embodiment: (a) ligating (120) a double stranded adaptor to an end of the polynucleotide (122), the end of the polynucleotide having a dephosphorylated 5' hydroxyl and the end of the double stranded adaptor (124) to be ligated having a first strand (126) and a second strand (128), the second strand of the double stranded adaptor having a 3' blocking group (130); (b) removing the 3' blocking group of the second strand after ligation, e.g. by washing (132), or by enzymatically or chemically removing the group in situ, e.g. by treatment with a phosphatase if the blocking group is a phosphate; (c) phosphorylating (134) the 5' hydroxyl of the polynucleotide; (d) ligating (136) a second strand (142) having an unblocked 3' moiety to regenerate the double stranded adaptor (138); and (e) identifying (144) one or more nucleotides at the end of the polynucleotide by the identity of the adaptor ligated thereto, e.g. via a fluorescent label (140), an encoded adaptor (described below), amplification (by providing a primer binding site), or the like. The double stranded adaptors and target polynucleotides may be combined for ligation either singly or as mixtures. For example, a single kind of adaptor having a defined sequence may be combined with a single kind of polynucleotide having a common (and perhaps, unknown) nucleotide sequence; or a single kind of adaptor having a defined sequence may be combined with a mixture of poly nucleotides, such as a plurality of uniform populations of identical polynucleotides attached to different solid phase supports in the same reaction vessel, e.g. described by Brenner et al, International application PCT/US96/09513; or a mixture of double stranded adaptors, particularly mixtures having different nucleotide sequences in their protruding strands, may be combined with a single kind of polynucleotide; or a mixture of double stranded adaptors may be combined with a mixture of polynucleotides. When the term "adaptor", or "double stranded adaptor," is used in the singular it is meant to encompass mixtures of adaptors having different sequences of protruding strands as well as a single kind of adaptor having the same sequence of protruding strand, in a manner analogous to the usage of the term "probe."

Figure 2B:
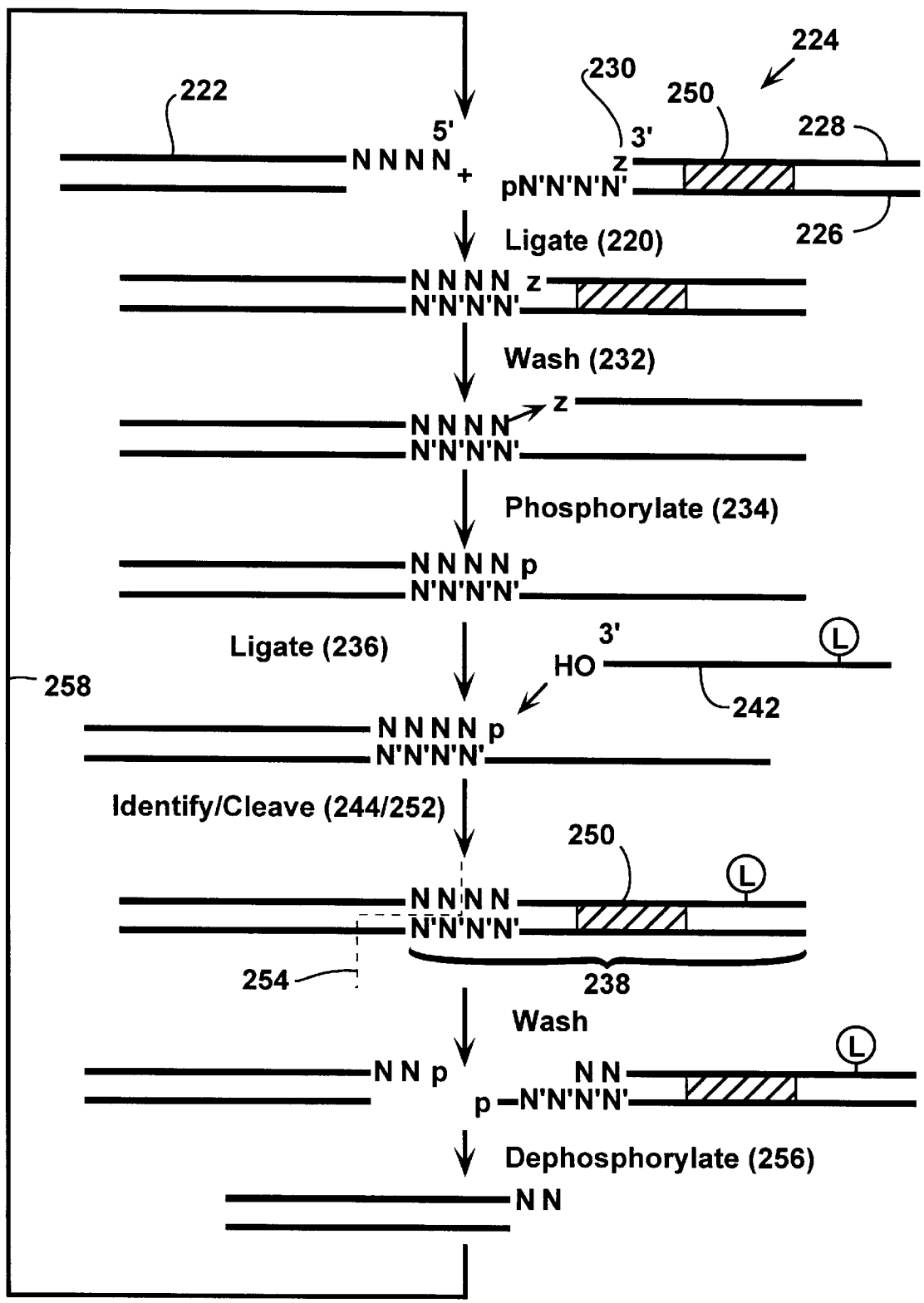
FIG. 2b illustrates the use of the preferred embodiment in a method of DNA sequencing by stepwise cycles of ligation and cleavage.
Figure 3A:
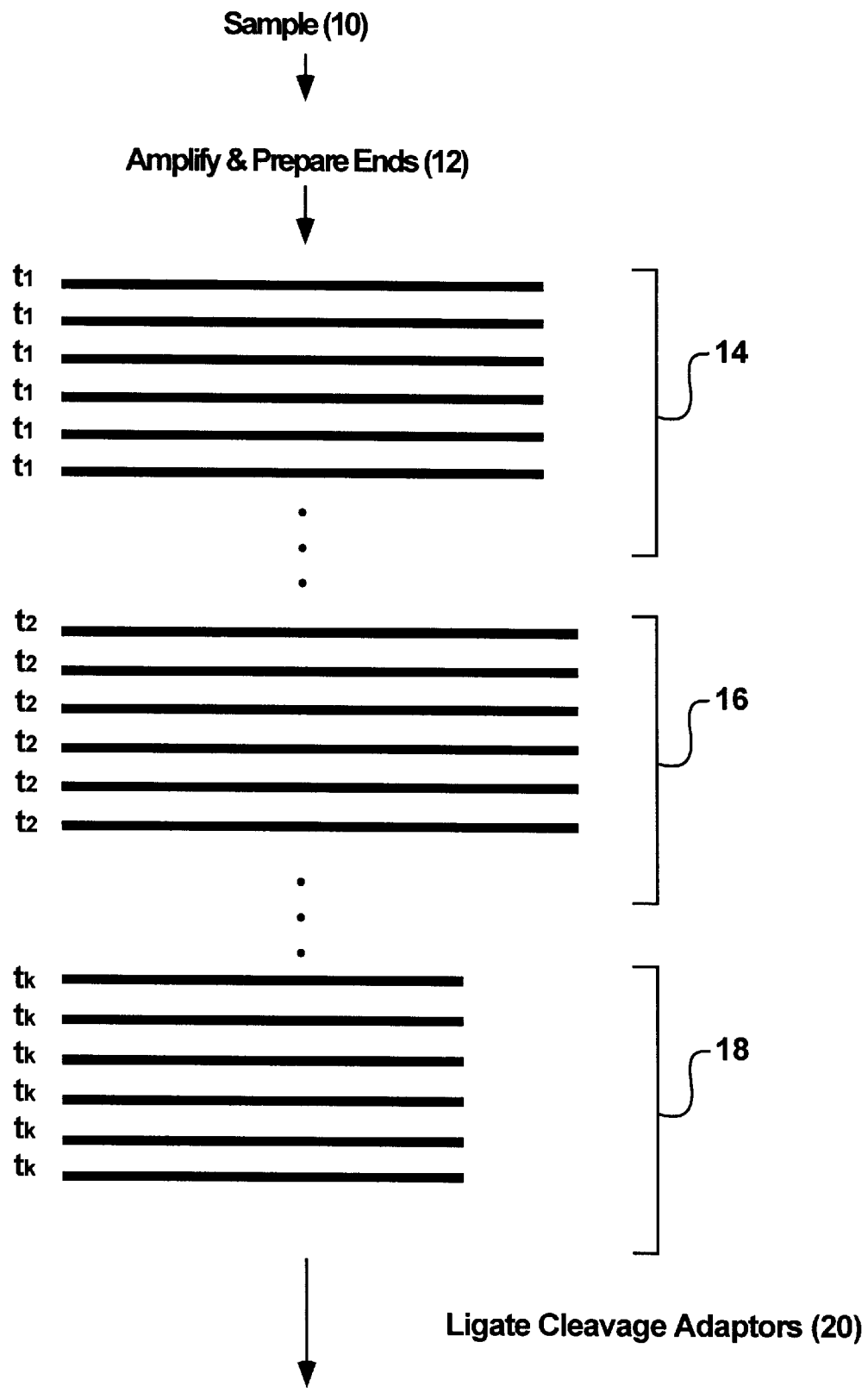
FIGS. 3a–3e illustrate an embodiment of the invention for DNA sequencing that does not require cycles of ligation and cleavage.
Figure 3B:
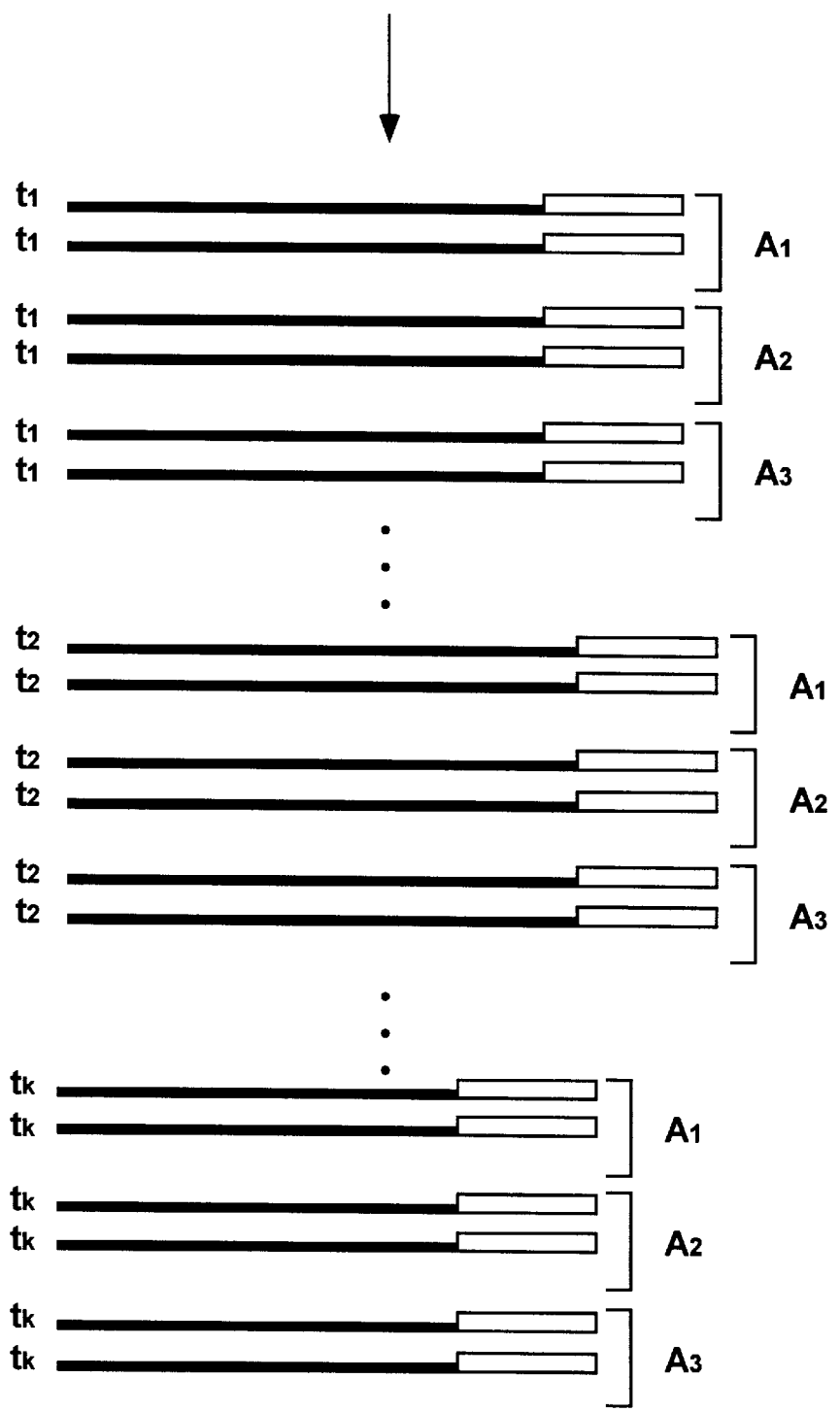
Figure 3C:
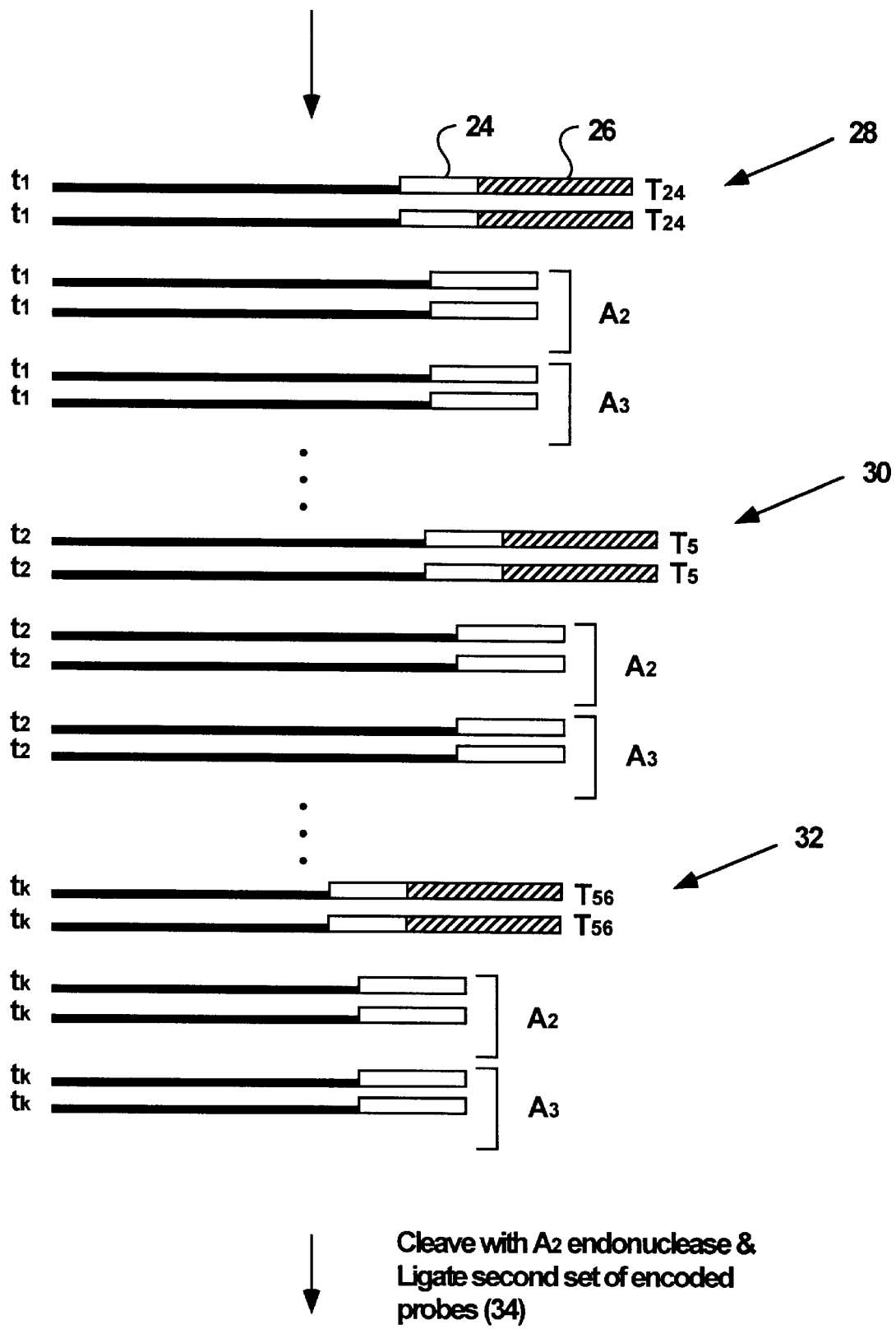
Figure 3D:
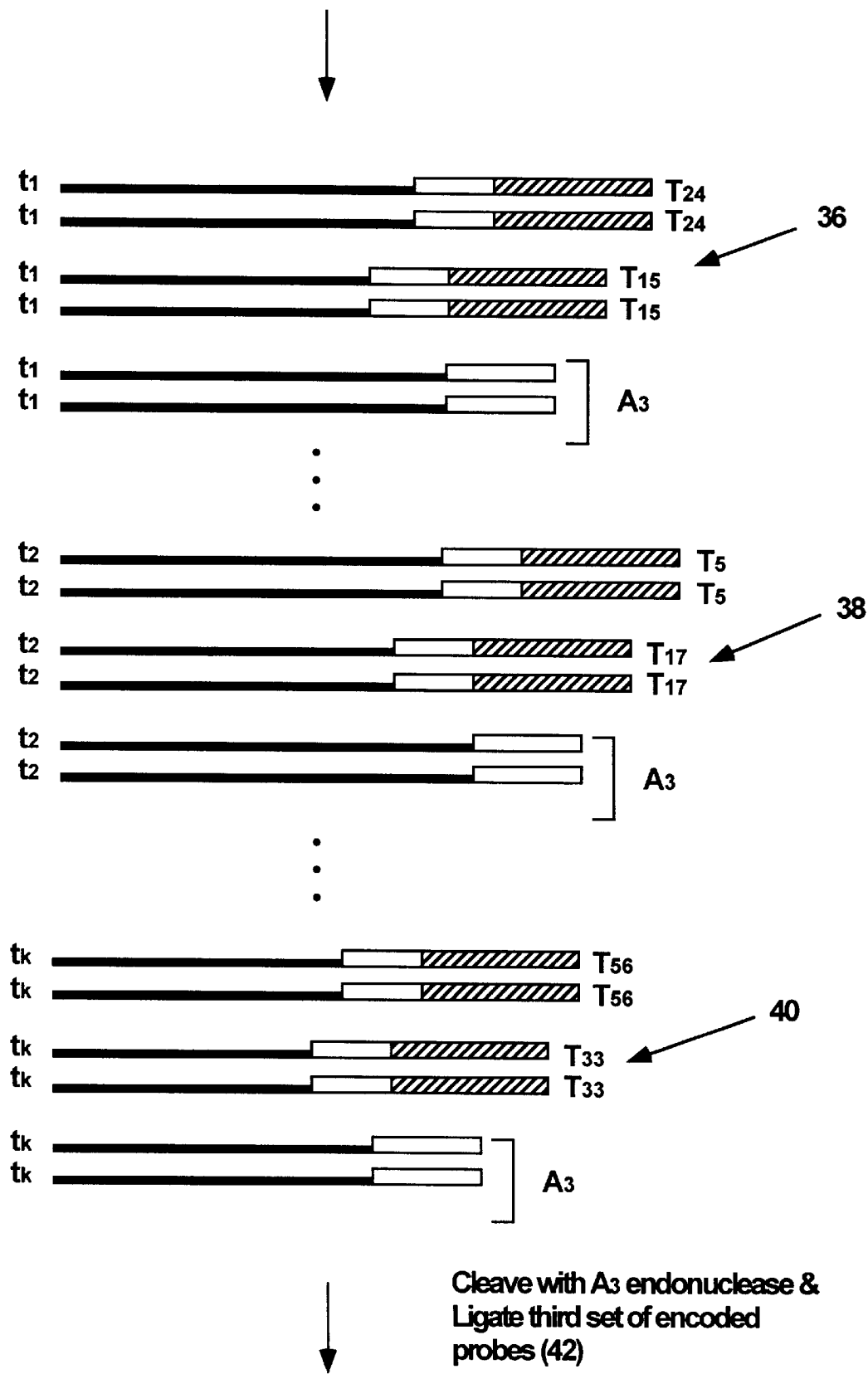
Figure 3E:
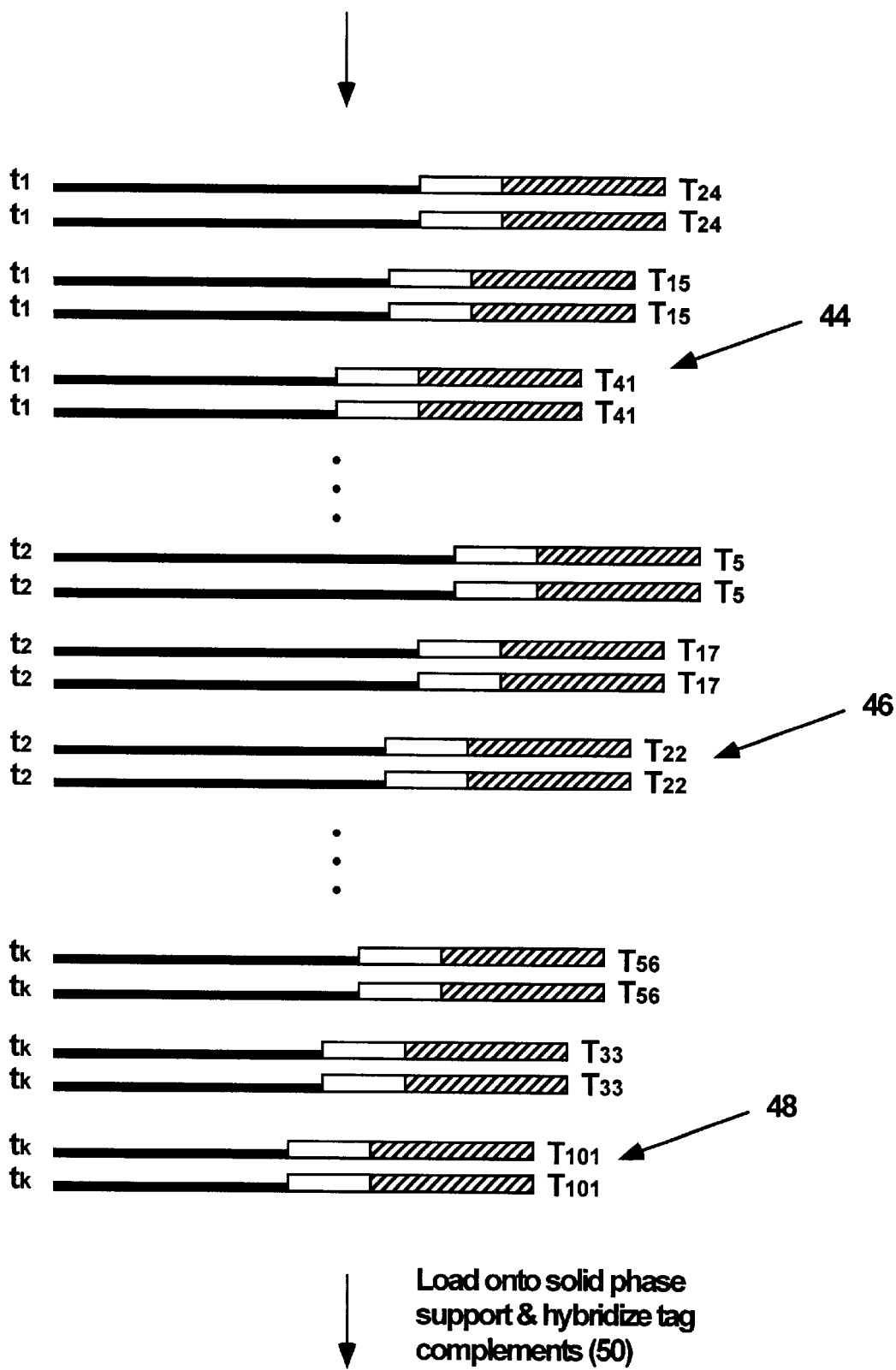

A preferred embodiment employing cycles of ligation and cleavage, such as illustrated in FIG. 2b, comprises the following steps: (a) ligating (220) a double stranded adaptor to an end of the polynucleotide (222), the end of the polynucleotide having a dephosphorylated 5' hydroxyl, the end of the double stranded adaptor to be ligated (224) having a first strand (226) and a second strand (228), the second strand of the double stranded adaptor having a 3' blocking group (230). and the double stranded adaptor having a nuclease recognition site (250) of a nuclease whose recognition site is separate from its cleavage site; (b) removing the 3' blocking group after ligation, e.g. by washing off the second strand (232); (c) phosphorylating (234) the 5' hydroxyl of the polynucleotide; (d) ligating (236) a second strand (242) having an unblocked 3' moiety to regenerate the double stranded adaptor (238) and the nuclease recognition site (250); (e) identifying (244) one or more nucleotides at the end of the polynucleotide by the identity of the adaptor ligated thereto; (f) cleaving (252) the polynucleotide with a nuclease that recognizes the recognition site such that the polynucleotide is shortened by one or more nucleotides, the recognition site being positioned in the illustrated adaptor (224) so that the cleavage (254) removes two nucleotides from polynucleotide (222); (g) dephosphorylating (256) the 5' end of the polynucleotide; and (h) repeating (258) steps (a) through (g).

Typically, prior to ligation, ends of polynucleotides to be analyzed are prepared by digesting them with one or more restriction endonucleases that produce predetermined cleavages, usually having 3' or 5' protruding strands. i.e. "sticky" ends. Such digestions usually leave the 5' strands phosphorylated. Preferably, these 5' phosphorylated ends are dephosphorylated by treatment with a phosphatase, such as calf intestinal alkaline phosphatase, or like enzyme, using standard protocols, e.g. as described in Sambrook et al, Molecular Cloning, Second Edition (Cold Spring Harbor Laboratory, New York, 1989). By removal of the 5' phosphates the target polynucleotides are rendered incapable of being ligated in the presence of a ligase. The step of dephosphorylating preferably leaves a free 5' hydroxyl.

Ligation of the double stranded adaptor to the dephosphorylated end of a polynucleotide may be carried out enzymatically or chemically, depending on the particular embodiment. Preferably, ligation is carried out enzymatically using a ligase in a standard protocol. Many ligases are known and are suitable for use in the invention, e.g. Lehman, Science, 186: 790–797 (1974); Engler et al, DNA Ligases, pages 3–30 in Boyer, editor, The Enzymes, Vol. 15B (Academic Press. New York, 1982); and the like. Preferred ligases include T4 DNA ligase. T7 DNA ligase, *E. coli* DNA ligase, Taq ligase, Pfu ligase, and Tth ligase. Protocols for their use are well known, e.g. Sambrook et al (cited above); Barany, PCR Methods and Applications, 1: 5–16 (1991); Marsh et al, Strategies, 5: 73–76 (1992); and the like. Generally, ligases require that a 5' phosphate group be present for ligation to the 3' hydroxyl of an abutting strand. Thus, whenever a ligase is employed to ligate a double stranded adaptor to a target polynucleotide, the 5' strand of the complementary end of the double stranded adaptor must be phosphorylated.

Generally, double stranded adaptors of the invention provide the same functions as the adaptors described in Unrau et al (cited above). Sibson (cited above), and Brenner (cited above), the latter of which is incorporated by reference for its description of adaptors (or as designated in that reference "probes") and for its description of their operation in DNA sequencing by stepwise ligation and cleavage. Adaptors provide a "platform" for carrying out either one or both of two operations: First, by specific hybridization of its (their) complementary protruding strand(s) to that (those) of a target polynucleotide, an adaptor (or sometimes a pair of adaptors) provide(s) a means for identifying one or more nucleotides in the protruding strand of the target polynucleotide or a means for classifying subpopulations of target polynucleotides, e.g. by providing primer binding sites for selective amplification, as described in Unrau et al (cited above). Second, an adaptor provides a recognition site from which a nuclease may cleave the target polynucleotide to which adaptor is ligated. As illustrated in Brenner (cited above), adaptors do not necessarily provide both functions in every embodiment.

In reference to the formula for the double stranded adaptors set forth above, preferably n is in the range of 2 to 6, inclusive; and r and q are separately in the range of 8 to 50, inclusive. The 3' blocking group "z" may have a variety of forms and may include almost any chemical entity that precludes ligation and that does not interfere with other steps of the method, e.g. removal of the 3' blocked strand, ligation, or the like. Exemplary 3' blocking groups include, but are not limited to, hydrogen (i.e. 3' deoxy), phosphate, phosphorothioate, acetyl, and the like. Preferably, the 3' blocking group is a phosphate because of the convenience in adding the group during the synthesis of the 3' blocked strand and the convenience in removing the group with a phosphatase to render the strand capable of ligation with a ligase. An oligonucleotide having a 3' phosphate may be synthesized using the protocol described in chapter 12 of Eckstein, Editor, Oligonucleotides and Analogues: A Practical Approach (IRL Press, Oxford, 1991).

Besides removing by melting, a 3' deoxy may be removed from a second strand by a polymerase "exchange" reaction disclosed in Kuijper et al, Gene, 112: 147–155 (1992); Aslanidis et al, Nucleic Acids Research. 18: 6069–6074 (1990); and like references. Briefly, the 5'→3' exonuclease activity of T4 DNA polymerase, and like enzymes, may be used to exchange nucleotides in a priming strand with their triphosphate counterparts in solution. Thus, with such a reaction a 3' dideoxynucleotide can be exchanged with a 2'-deoxy-3'-hydroxynucleotide from a reaction mixture, which would render the second strand ligatable to the target polynucleotide after treatment with a polynucleotide kinase.

Further 3' blocking groups are available from the chemistries developed for reversable chain terminating nucleotides in base-by-base sequencing schemes, e.g. disclosed in the following references: Cheeseman, U.S. Pat. No. 5,302,509: Tsien et al. International application WO 91/06678: Canard et al, Gene, 148: 1–6 (1994); and Metzker et al, Nucleic Acids Research, 22: 4259–4267 (1994). Roughly, these chemistries permit the chemical or enzymatic removal of specific blocking groups (usually having an appendent lablel) to generative a free hydroxyl at the 3' end of a priming strand.

The complementary strands of the adaptors are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. Nos. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the ligation and cleavage reagents. After synthesis, the complementary strands are combined to form a double stranded adaptor. The protruding strand of a adaptor may be synthesized as a mixture, such that every possible sequence is represented in the protruding portion, as described in Brenner (cited above).

As also explained in Brenner (cited above), it is not critical whether protruding strand of the adaptor is a 5' or 3' end. However, it is important that the protruding strands of the target polynucleotide and adaptors (or at least one of a mixture applied to the target polynucleotide) be capable of forming perfectly matched duplexes to allow for specific hybridization and ligation. If the protruding strands of the target polynucleotide and adaptor are different lengths the resulting gap can be filled in by a polyrnerase prior to ligation, e.g. as in "gap LCR" disclosed in Backmnan et al, European patent application 91100959.5. Such aap filling can be used as a means for identifying one or more nucleotides in the protruding strand of the target polynucleotide. Preferably, the number of nucleotides in the respective protruding strands are the same so that both strands of the adaptor and target polynucleotide are capable of being ligated without a filling step. Preferably, the protruding strand of the adaptor is from 2 to 6 nucleotides long.

As mentioned above, a preferred double stranded adaptor is defined by the formula:

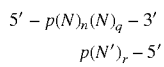

or

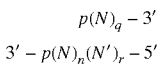

where preferred values for p, N, N', n, q, and r are as defined above. More preferably, n is in the range of from 2 to 5; and q and r are in the range of from 12 to 50, and may be the same or different. Most preferably, n is 4. A 5' monophosphate can be attached either chemically or enzymatically with a kinase, e.g. Sambrook et al, Molecular Cloning: A Laboratory Manual, 2nd Edition (Cold Spring Harbor Laboratory, New York, 1989). Chemical phosphorylation is described by Horn and Urdea, Tetrahedron Lert., 27: 4705 (1986), and reagents for carrying out the disclosed protocols are commercially available, e.g. 5' Phosphate-ON™ from Clontech Laboratories (Palo Alto, Calif.).

The adaptors of the invention can be labeled in a variety of ways, including the direct or indirect attachment of radioactive moieties, fluorescent moieties, calorimetric moieties, and the like, as disclosed in Brenner (cited above), which is incorporated by reference for its description of labeling modalities for adaptors. Preferably, the adaptors are labeled with one or more fluorescent dyes, e.g. as disclosed by Menchen et al, U.S. Pat. No. 5,188,934; Begot et al PCT application PCT/US90/05565. Pairs of dyes using fluorescence energy transfer may be employed on each adaptor as taught by Ju et al, Proc. Natl. Acad. Sci., 92: 4347–4351 (1995) and Ju et al, Nature Medicine, 2: 246–249 (1996).

In some embodiments, it may be desirable to use one or two signal generating moieties, such as one or two types of fluorescent dye, in a sequencing operation. Under such conditions, a sequence can be characterized by the presence or absence of a particular nucleotide at consecutive locations along a polynucleotide. For example, the sequence, "acg-gaaat" can be described in terms of the presence and absence of t's, expressed as: "(not t)-(not t)-(not t)-(not t)-tt-(not t)-(not t)-t". Or, such a sequence may be described in terms of the presence and absence of purines, expressed as: "purine-(not purine)-purine-purine-(not purine)-(not purine)-purine-purine-(not purine)". Preferably, two dyes are employed in such embodiments so that a positive signal is measured, even to show the absence of a particular nucleotide or base. Such binary sequences may be used to uniquely identify polynucleotides from a population, such as a cDNA library, provided the sequence is long enough.

A single signal generating moiety, such as a single fluorescent dye, may be employed when sequencing several different target pol%nucleotides attached to different spatially addressable solid phase supports, in a parallel sequencing operation such as described in International patent application PCT/US95/12791. This may be accomplished by providing four sets of adaptors that would be applied sequentially to the plurality of target polynucleotides. Exemplary set of such adaptors are shown below:

a second nuclease. The nucleases are selected to leave identical kinds of overhangs after cleavage. Adaptors of each set are labeled either with a first label or a second label depending on whether they are designed to produce a successful ligation in the presence of A or G, respectively, for the first set, or in the presence of C or T, respectively, for the second set. The adaptors of both sets are applied to a collection of immobilized target polynucleotides with an appropriate protruding strand and ligated in accordance with the invention. The positions and characteristics, e.g. colors, of the signals generated by the labels are recorded. Next, the ligated adaptors are cleaved with the first nuclease and washed. The sites where the signals disappear correspond to sites where A's and G's were present in the target polynucleotide and the sites where the signals remain correspond to sites with C's and T's present in the target polynucleotide. The adaptors are then cleaved with the second nuclease to complete the cycle of ligation and nuclease cleavage.

| Set1 | Set2 | Set3 | Set4 |
|---|---|---|---|
| ANNNN...NN<br>N...NNTT...T* | dANNNN...NN<br>d N...NNTT...T | dANNNN...NN<br>N...NNTT...T | dANNNN...NN<br>N...NNTT...T |
| dCNNNN...NN<br>N...NNTT...T | CNNNN...NN<br>N...NNTT...T* | dCNNNN...NN<br>N...NNTT...T | dCNNNN...NN<br>N...NNTT...T |
| dGNNNN...NN<br>N...NNTT...T | dGNNNN...NN<br>N...NNTT...T | GNNNN...NN<br>N...NNTT...T* | dGNNNN...NN<br>N...NNTT...T |
| dTNNNN...NN<br>N...NNTT...T | dTNNNN...NN<br>N...NNTT...T | dTNNNN...NN<br>N...NNTT...T | TNNNN...NN<br>N...NNTT...T* | where each of the listed adaptors represents a mixture of $4^3$=64 oligonucleotides such that the identity of the 3' terminal nucleotide of the top strand is fixed and the other positions in the protruding strand are filled by every permutation of a sequence of three nucleotides, or complexity reducing analogs. The listed adaptors are also shown with a single stranded poly-T tail with a signal generating moiety attached to the terminal thymidine, shown as "T*". The "d" on the unlabeled adaptors designates a ligation-blocking moiety or absence of 3'-hydroxyl, which prevents unlabeled adaptors from being ligated. Preferably, such 3'-terminal nucleotides are dideoxynucleotides. In this embodiment, the adaptors of set 1 are first applied to a plurality of target polynucleotides and treated with a ligase so that target polynucleotides having a thymidine complementary to the 3' terminal adenosine of the labeled adaptors are ligated. The unlabeled adaptors are simultaneously applied to minimize inappropriate ligations. The locations of the target polynucleotides that form ligated complexes with adaptors terminating in "A" are identified by the signal generated by the label carried on the adaptor. After washing and cleavage, the adaptors of set 2 are applied. In this case, target polynucleotides forming ligated complexes with adaptors terminating in "C" are identified by location. Similarly, the adaptors of sets 3 and 4 are applied and locations of positive signals identified. The process of sequentially applying the four sets of adaptors continues until the desired number of nucleotides are identified on the target polynucleotides.

In another embodiment, two labels, e.g. fluorescent dyes, may be employed to alternatively identify purines and pyrimidines in a parallel DNA sequencing scheme such as described in International patent application PCT/US95/12791. Two sets of adaptors are provided having recognition sites for different type IIs nucleases, i.e. a first nuclease and Olizonucleotide Tags and Encoded Adaptors Using encoded adaptors, a target polynucleotide may be analyzed based on a single ligation of one or more sets of encoded adaptors to its terminus (or to the termini of multiple target polynucleotides when used in a parallel sequencing operation). That is, cycles of ligation and cleavage may be used, but are not required. As used herein the term "encoded adaptor" means a double stranded adaptor as described above which includes an oligonucleotide tag selected from a minimally cross-hybridizing set of oligonucleotides. Encoded adaptors whose protruding strands form perfectly matched duplexes with the complementary protruding strands of the target polynucleotide are ligated in accordance with the invention. After ligation, the identity and ordering of the nucleotides in the protruding strands are determined, or "decoded," by specifically hybridizing a labeled tag complement to its corresponding tag on the ligated adaptor.

For example, if an encoded adaptor with a protruding strand of four nucleotides, say 5'-AGGT, forms a perfectly matched duplex with the complementary protruding strand of a target polynucleotide and is ligated, the four complementary nucleotides, 3'-TCCA, on the polynucleotide are identified by a unique oligonucleotide tag selected from a set of 256 such tags, one for every possible four nucleotide sequence of the protruding strands. Tag complements are applied to the ligated adaptors under conditions which allow specific hybridization of only those tag complements that form perfectly matched duplexes (or triplexes) with the oligonucleotide tags of the ligated adaptors. The tag complements may be applied individually or as one or more mixtures to determine the identity of the oligonucleotide tags, and therefore, the sequence of the protruding strands. As explain more fully below, successive sets of encoded adaptors are preferably applied to the target polynucleotides such that each set is capable of identifying the nucleotide sequence of a different portion of a target polynucleotide.

An important feature of the encoded adaptors is the use of oligonucleotide tags that are members of a minimally cross-hybridizing set of oligonucleotides, e.g. as described in International patent application PCT/US96/09513 and U.S. Pat. No. 5,604,097, the latter of which is incorporated by reference for its description of oligonucleotide tags. The sequences of oligonucleotides of such a set differ from the sequences of every other member of the same set by at least two nucleotides. Thus, each member of such a set cannot form a duplex (or triplex) with the complement of any other member with less than two mismatches. Preferably, each member of a minimally cross-hybridizing set differs from every other member by as many nucleotides as possible consistent with the size of set required for a particular application. For example, where longer oligonucleotide tags are used, such as 12- to 20-mers for delivering labels to encoded adaptors, then the difference between members of a minimally cross-hybridizing set is preferably significantly greater than two. Preferably, each member of such a set differs from every other member by at least four nucleotides. More preferably, each member of such a set differs from every other member by at least six nucleotides. Complements of oligonucleotide tags of the invention are referred to herein as "tag complements."

Oligonucleotide tags may be single stranded and be designed for specific hybridization to single stranded tag complements by duplex formation. Oligonucleotide tags may also be double stranded and be designed for specific hybridization to single stranded tag complements by triplex formation.

Multiple sets of encoded adaptors may be employed which are ligated to a target polynucleotide at staggered cleavage points so that the encoded adaptors provide sequence information from each of a plurality of contiguous portions of the target polynucleotide. Such contiguous portions preferably correspond to protruding strands of the target polynucleotide generated in the method.

The invention makes use of nucleases whose recognition sites are separate from their cleavage sites. As explained more fully below, such nucleases are preferably type IIs restriction endonucleases. The nucleases are used to generate protruding strands on target polynucleotides to which encoded adaptors are ligated. The amount of sequence information obtained in a given embodiment of the invention depends in part on how many such nucleases are employed and the length of the protruding strand produce upon cleavage.

An important aspect of the invention is the capability of sequencing many target polynucleotides in parallel. In this aspect, the method of the invention comprises the following steps: (a) attaching a first oligonucleotide tag from a repertoire of tags to each polynucleotide in a population of polynucleotides such that each first oligonucleotide tag from the repertoire is selected from a first minimally cross-hybridizing set; (b) sampling the population of polynucle-otides such that substantially all different polynucleotides in the population have different first oligonucleotide tags attached; (c) ligating one or more encoded adaptors to an end of the polynucleotides in the population, the polynucleotides having dephosphorylated 5' ends, and each encoded adaptor having a 3' blocking group, a second oligonucleotide tag selected from a second minimally cross-hybridizing set, and a protruding strand complementary to a protruding strand of a polynucleotide of the population; (d) sorting the polynucleotides from the population by specifically hybridizing the first oligonucleotide tags with their respective complements, the respective complements being attached as uniform populations of substantially identical oligonucleotides in spatially discrete regions on the one or more solid phase supports; and (e) identifying a plurality of nucleotides in said protruding strands of the polynucleotides by specifically hybridizing a tag complement to each second oligonucleotide tag of the one or more encoded adaptors.

The above aspect of the invention is illustrated by an embodiment shown in FIGS. 3a through 3e. In this embodiment, k target polynucleotides are prepared as described below, and in Brenner, International patent application PCT/US95/12791. That is, a sample is taken from a population of polynucleotides conjugated with oligonucleotide tags designated by small "t's." These tags are sometimes referred to as oligonucleotide tag for sorting, or as "first" oligonucleotide tags. The tag-polynucleotide conjugates of the sample are amplified, e.g. by polymerase chain reaction (PCR) or by cloning, to give 1 through k populations of conjugates, indicated by (14)–(18) in FIG. 3a. Preferably, the ends of the conjugates opposite that of the (small "t") tags are prepared for ligating one or more adaptors, each of which contains a recognition site for a nuclease whose cleavage site is separate from its recognition site. In the illustrated embodiment, three such adaptors, referred to herein as "cleavage adaptors," are employed. The number of such adaptors employed depends on the amount of sequence information desired. Preferably, from one to three cleavage adaptors are used.

If the method of the invention is being applied to signature sequencing of a cDNA population, then prior to ligation of the cleavage adaptors, the tag-polynucleotide conjugates may be cleaved with a restriction endonuclease with a high frequency of recognition sites, such as Taq I, Alu I, HinP1 I, or the like. For enzymes, such as Alu I, that leave blunt ends, a staggered end may be produced with T4 DNA polymerase, e.g. as described in Brenner, International patent application PCTIUS95/12791, and Kuijper et al, Gene, 112: 147–155 (1992). If the target polynucleotides are prepared by cleavage with Taq I, then the following ends are available for ligation:

```
          cgannnn ... -3'
             tnnnn ... -5'
```

Thus, an exemplary set of three cleavage adaptors may be constructed as follows:

```
(1)  NN ... NGAAGA          cgannnnnnnnnnnnnnnnnnn ... -3'
     NN ... NCTTCTGCp           tnnnnnnnnnnnnnnnnnnnn ... -5'

(2)  NN ... NGCAGCA          cgannnnnnnnnnnnnnnnnnn ... -3'
     NN ... NCGTCGTGCp          tnnnnnnnnnnnnnnnnnnnn ... -5'
```

-continued

```
(3)  NN ... NGGGA       cgannnnnnnnnnnnnnnnnn ... -3'
     NN ... NCCCTGCp    tnnnnnnnnnnnnnnnnnnnn ... -5'
``` where cleavage adaptors (1), (2), and (3) are shown in capital letters with the respective recognition sites of nucleases Bbs I, Bbv I, and Bsm FI underlined and a 5' phosphate indicated as "p." The double underlined portions of the target polynucleotide indicate the positions of the protruding strands after ligation and cleavage. In all cases, the target polynucleotide is left with a 5' protruding strand of four nucleotides. Clearly, many different embodiments can be constructed using different numbers and kinds of nucleases.

Returning to the illustrated embodiment, cleavage adaptors $A_1$, $A_2$, and $A_3$ are ligated (20) in a concentration ratio of 1:1:1 to the k target polynucleotides to give the conjugates shown in FIG. 1b, such that within each population of tag-polynucleotide conjugates there are approximately equal numbers of conjugates having $A_1$, $A_2$, and $A_3$ attached. After ligation (20), the target polynucleotides are successively cleaved with each of the nucleases of the cleavage adaptors and ligated to a set of encoded adaptors. First, the target polynucleotides are cleaved (22) with the nuclease of cleavage adaptor $A_1$ after which a first set of encoded adaptors are ligated to the resulting protruding strands. The cleavage results in about a third of the target polynucleotides of each type, i.e. $t_1, t_2, \ldots t_k$, being available for ligation. Preferably, the encoded adaptors are applied as a mixture of adaptors which contain every possible sequence of protruding strand. Reaction conditions are selected so that only encoded adaptors whose protruding strands form perfectly matched duplexes with those of the target polynucleotide are ligated to form encoded conjugates (28), (30), and (32). The capital "T's" with subscripts indicate that unique oligonucleotide tags are carried by the encoded adaptors for labeling. The oligonucleotide tags carried by encoded adaptors are sometimes referred to tags for delivering labels to the encoded adaptors, or as "second" oligonucleotide tags. As described more fully below, single stranded oligonucleotide tags used for sorting preferably consist of only three of the four nucleotides, so that a T4 DNA polymerase "stripping" reaction can be used to prepare target polynucleotides for loading onto solid phase supports. On the other hand, oligonucleotide tags employed for delivering labels may consist of all for nucleotides.

As mentioned above, encoded adaptors comprise a protruding strand (24) and an oligonucleotide tag (26). Thus, if the "$A_1$" cleavage of the $t_1$-polynucleotide conjugates resulted in the following ends:

```
5'- ... nnnnnnnnn
3'- ... nnnnnnnnnacct
``` then oligonucleotide tag $T_{24}$ could have the following structure (SEQ ID NO: 1):

```
tggattctagagagagagagagagagag -3'
   aagatctctctctctctctctctc
``` where the double stranded portion may be one of a set of 768 (=3×256) double stranded 20-mer oligonucleotide tags that forms a perfectly matched triplex with a unique tag complement and forms a triplex with at least 6 mismatches with all other tag complements. Optionally, an encoded adaptor may also comprise a spacer region, as shown in the above example where the 4 nucleotide sequence "ttct" serves as a spacer between the protruding strand and the oligonucleotide tag.

After ligation of the first set of encoded adaptors (28), (30), and (32), the tag-polynucleotide conjugates are cleaved (34) with the nuclease of cleavage adaptor $A_2$, after which a second set of encoded adaptors is applied to form conjugates (36), (38), and (40). Finally, the tag-polynucleotide conjugates are cleaved (42) with the nuclease of cleavage adaptor $A_3$, after which a third set of encoded adaptors is applied to form conjugates (44), (46), and (48). After completion of the succession of cleavages and ligations of encoded adaptors, the mixture is loaded (50) onto one or more solid phase supports via oligonucleotide tags $t_1$ through $t_k$ as described more fully below, and as taught by Brenner (cited above). It should be clear that if a single target polynucleotide were being analyzed. then multiple oligonucleotide tags, $t_1, t_2, \ldots t_k$, would not be necessary. In such an embodiment, a biotin, or like moiety, could be employed to anchor the polynucleotide-encoded adaptor conjugate, as no sorting would be required.

Sequence information is obtained by successively applying labeled tag complements, either individually or as mixtures. Preferably, for the embodiment illustrated in FIGS. 3a through 3e, the tag complements are applied successively in 12 mixtures of 64 tag complements each. Within each mixture there are four separate subsets of tag complements, each with a different fluorescent label. The four subsets correspond to tag complements which decode or identify one of the four nucleotides at a given position in the protruding strand (to which the encoded adaptor was ligated). For example, a mixture of 64 tag complements may identify nucleotide "x" in the protruding strand sequence "nnxn" so that a first fluorescent label is observed if x=A, a second fluorescent label is observed if x=C, a third fluorescent label is observed if x=G, and so on. Four of the 12 mixtures is for identifying the nucleotides in the protruding strands produced by cleavage with the nuclease of cleavage adaptor $A_1$, four are for identifying the nucleotides in the protruding strands produced by cleavage with the nuclease of cleavage adaptor $A_2$, and four are for identifying the nucleotides in the protruding strands produced by cleavage with the nuclease of cleavage adaptor $A_3$.

Further sequence information can be obtained using the embodiment described above in a process analogous to the "multi-stepping" process disclosed in Brenner, International patent application PCT/US95/03678. In this embodiment, a fourth adaptor, referred to herein as a "stepping adaptor," is ligated to the ends of the target polynucleotides along with cleavage adaptors $A_1$, $A_2$, and $A_3$, for example, in a concentration ratio of 3:1:1:1. Thus, approximately half of the available ends are ligated to the stepping adaptor. The stepping adaptor includes a recognition site for a type IIs nuclease positioned such that its reach (defined below) will permit cleavage of the target polynucleotides at the end of the sequence determined via cleavage adaptors $A_1$, $A_2$, and $A_3$. An example of a stepping adaptor that could be used with the above set of cleavage adaptors is as follows:

```
NN ... NCTGGAGA      cgannnnnnnnnnnnnnnnnnn ... -3'
NN ... NGACCTCTGCp   tnnnnnnnnnnnnnnnnnnnn ... -5'
``` where, as above, the recognition site of the nuclease, in this case BpM I, is singly underlined and the nucleotides at the cleavage site are doubly underlined. The target polynucleotides cleaved with the nuclease of the stepping adaptor may be ligated to a further set of cleavage adaptors $A_4$, $A_5$, and $A_6$, which may contain nuclease recognition sites that are the same or different than those contained in cleavage adaptors $A_1$, $A_2$, and $A_3$. Whether or not an enlarged set of encoded adaptors is required depends on whether cleavage and ligation reactions can be tolerated in the signal measurement apparatus. If, as above, it is desired to minimize enzyme reactions in connection with signal measurement, then additional sets of encoded adaptors must be employed. That is, where above 768 oligonucleotide tags and tag complements were called for, with six cleavage reactions producing protruding strands of four nucleotides each, 1536 oligonucleotide tags and tag complements (24 mixtures of 64 tag complements each) would be required. Exemplary, cleavage adaptors $A_4$, $A_5$, and $A_6$, with the same nuclease recognition sites as $A_1$, $A_2$, and $A_3$, and which could be used with the stepping adaptor shown above are as follows:

```
(4) NN ... NGAAGACNN   nnnnnnnnnnnnnnnnn ... -3'
    NN ... NCTTCTGp    nnnnnnnnnnnnnnnnnn ... -5'
(5) NN ... NGCAGCACNN  nnnnnnnnnnnnnnnnn ... -3'
    NN ... NCGTCGTGp   nnnnnnnnnnnnnnnnnn ... -5'
(6) NN ... NGGGACNN    nnnnnnnnnnnnnnnnn ... -3'
    NN ... NCCCTGp     nnnnnnnnnnnnnnnnnn ... -5'
``` where the cleavage sites are indicated by double underlining. Cleavage adaptors $A_4$, $A_5$, and $A_6$ are preferably applied as mixtures, such that every possible two-nucleotide protruding strand is represented.

Once the encoded adaptors have been ligated, the target polynucleotides are prepared for loading onto solid phase supports, preferably microparticles, as disclosed in Brenner. International patent application PCT/US95/12791. Briefly, the oligonucleotide tags for sorting are rendered single stranded using a "stripping" reaction with T4 DNA polymerase, discussed more fully below. The single stranded oligonucleotide tags are specifically hybridized and ligated to their tag complements on microparticles. The loaded microparticles are then analyzed in an instrument, such as described in Brenner (cited above) which permits the sequential delivery, specific hybridization, and removal of labeled tag complements to and from encoded adaptors.

Encoded adaptors may be used with the sorting methodology described in Brenner et al (cited above), to carry out shotgun sequencing on target polynucleotides from a few kilobases to a few tens of kilobases in length, e.g. 10–25 kilobases, when 12–16 nucleotides are identified in each of ten to fifty thousand fragments.

Synthesis of Adaptors

The encoded adaptors and cleavage adaptors are conveniently synthesized on automated DNA synthesizers using standard chemistries, such as phosphoramidite chemistry. e.g. disclosed in the following references: Beaucage and Iyer, Tetrahedron, 48: 2223–2311 (1992); Molko et al, U.S. Pat. No. 4,980,460; Koster et at U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the ligation and cleavage reagents. After synthesis of complementary strands, the strands are combined to form a double stranded adaptor. The protruding strand of an encoded adaptor may be synthesized zig a mixture, such that every possible sequence is represented in the protruding portion. Such mixtures are readily synthesized using well known techniques, e.g. as disclosed in Telenius et al, Genomics, 13: 718–725 (1992); Welsh et al, Nucleic Acids Research, 19: 5275–5279 (1991); Grothues et al, Nucleic Acids Research. 21: 1321–1322 (1993); Hartley, European patent application 90304496.4; and the like. Generally, these techniques simply call for the application of mixtures of the activated monomers to the growing oligonucleotide during the coupling steps where one desires to introduce multiple nucleotides. As discussed above, in some embodiments it may be desirable to reduce the complexity of the adaptors. This can be accomplished using complexity reducing analogs, such as deoxyinosine, 2-aminopurine, or the like, e.g. as taught in Kong Thoo Lin et al, Nucleic Acids Research, 20: 5149–5152, or by U.S. Pat. No. 5,002,867; Nichols et al, Nature. 369: 492–493 (1994); and the like.

In some embodiments, it may be desirable to synthesize encoded adaptors or cleavage adaptors as a single polynucleotide which contains self-complementary regions. After synthesis, the self-complementary regions are allowed to anneal to form a adaptor with a protruding strand at one end and a single stranded loop at the other end. Preferably, in such embodiments the loop region may comprise from about 3 to 10 nucleotides, or other comparable linking moieties, e.g. alkylether groups, such as disclosed in U.S. Pat. No. 4,914,210. Many techniques are available for attaching reactive groups to the bases or internucleoside linkages for labeling, as discussed in the references cited below.

When conventional ligases are employed in the invention, as described more fully below, the 5' end of the adaptor may be phosphorylated in some embodiments. A 5' monophosphate can be attached to a second oligonucleotide either chemically or enzymatically with a kinase, e.g. Sambrook et al, Molecular Cloning: A Laboratory Manual, 2nd Edition (Cold Spring Harbor Laboratory, New York, 1989). Chemical phosphorylation is described by Horn and Urdea, Tetrahedron Lett., 27: 4705 (1986), and reagents for carrying out the disclosed protocols are commercially available, e.g. 5' Phosphate-ON™ from Clontech Laboratories (Palo Alto, Calif.).

Preparation of Target Polynucleotides

Preferably, a target polynucleotide for use in the invention is double stranded and is prepared so that it has one or more protruding strands. The protruding strand may be either 5' or 3' and, preferably, the number of nucleotides in the protruding portion of the strand is in the range of from 2 to 6. A target polynucleotide is referred to as "−k" where k is some integer. e.g. usually between 2 and 6, whenever the 5' strand is protruding. Conversely, a target polynucleotide is referred to as "+k" whenever the 3' strand is protruding. For example the following would be a −4 target polynucleotide in accordance with this nomenclature:

```
5'-AACGTTTAC ...
       AAATG ...
```

In one preferred embodiment of the invention, the target polynucleotide is anchored to a solid phase support, such as a magnetic particle, polymeric microsphere, filter material, or the like, which permits the sequential application of reagents without complicated and time-consuming purification steps. The length of the target polynucleotide can vary widely; however, for convenience of preparation, lengths employed in conventional sequencing are preferred. For example, lengths in the range of a sew hundred basepairs, 200–300, to 1 to 2 kilobase pairs are preferred.

The target polynucleotides can be prepared by various conventional methods. For example, target polynucleotides can be prepared as inserts of any of the conventional cloning vectors, including those used in conventional DNA sequencing. Extensive guidance for selecting and using appropriate cloning vectors is found in Sambrook et al, Molecular Cloning: A Laboratory Manual, Second Edition (Cold Spring Harbor Laboratory, New York, 1989), and like references. Sambrook et al and Innis et al, editors, PCR Protocols (Academic Press, New York, 1990) also provide audience for using tolymerase chain reactions to prepare target polynucleotides. Preferably, cloned or PCR-amplified target polynucleotides are prepared which permit attachment to magnetic beads, or other solid supports, for ease of separating the target polynucleotide from other reagents used in the method. Protocols for such preparative techniques are described fully in Wahlberg et al, Electrophoresis, 13: 547–551 (1992); Tong et al, Anal. Chem., 64: 2672–2677 (1992); Hultman et al, Nucleic Acids Research, 17: 4937–4946 (1989); Hultman et al, Biotechniques. 10: 84–93 (1991); Syvanen et al, Nucleic Acids Research, 16: 11327–11338 (1988); Dattagupta et al, U.S. Pat. No. 4,734, 363; Uhlen, PCT application PCT/GB89/00304; and like references. Kits are also commercially available for practicing such methods, e.g. Dynabeads™ template preparation kit from Dynal AS. (Oslo, Norway).

Populations of target polynucleotides may be prepared in parallel by the use of microparticles, e.g. magnetic beads, controlled pore glass particles, or the like, that each have a uniform population of identical minimally cross-hybridizing oligonucleotides attached, as described in Brenner et al, International application PCT/US96/09513.

"Nuclease" as the term is used in accordance with the invention means any enzyme, combination of enzymes, or other chemical reagents, or combinations chemical reagents and enzymes that when applied to a ligated complex, discussed more fully below, cleaves the ligated complex to produce an augmented adaptor and a shortened target polynucleotide. A nuclease of the invention need not be a single protein, or consist solely of a combination of proteins. A key feature of the nuclease, or of the combination of reagents employed as a nuclease, is that its (their) cleavage site be separate from its (their) recognition site. The distance between the recognition site of a nuclease and its cleavage site will be referred to herein as its "reach." By convention, "reach" is defined by two integers which give the number of nucleotides between the recognition site and the hydrolyzed phosphodiester bonds of each strand. For example, the recognition and cleavage properties of Folk is typically represented as "GGATG(9/13)" because it recognizes and cuts a double stranded DNA as follows (SEQ ID NO: 2):

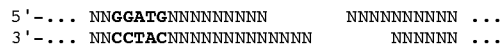

where the bolded nucleotides are Fok I's recognition site and the N's are arbitrary nucleotides and their complements.

It is important that the nuclease only cleave the target polynucleotide after it forms a complex with its recognition site; and preferably, the nuclease leaves a protruding strand on the target polynucleotide after cleavage.

Preferably, nucleases employed in the invention are natural protein endonucleases (i) whose recognition site is separate from its cleavage site and (ii) whose cleavage results in a protruding strand on the target polynucleotide. Most preferably, class IIs restriction endonucleases are employed as nucleases in the invention, e.g. as described in Szybalski et al. Gene. 100: 13–26 (1991); Roberts et al, Nucleic Acids Research, 21: 3125–3137 (1993); and Livak and Brenner U.S. Pat. No. 5,093,245. Exemplary class IIs nucleases for use with the invention include Alw XI, Bsm AI, Bbv I, Bsm FI, Sts I, Hga I, Bsc AI, Bbv II, Bce fI, Bce 85I, Bcc I, Bcg I, Bsa I, Bsg I, Bsp MI, Bst 71 I, Ear I, Eco 57I, Esp 3I, Fau I, Fok I, Gsu I, Hph I, Mbo II, Mme I, Rle Al, Sap I, Sfa NI, Taq II, Tth 111 II, Bco 5I, Bpu AI, Fin I, Bsr DI, and isoschizomers thereof. The preferred nuclease is Bbv I.

Preferably, prior to nuclease cleavage steps, usually at the start of a sequencing operation, the target polynucleotide is treated to block the recognition sites and/or cleavage sites of the nuclease being employed. This prevents undesired cleavage of the target polynucleotide because of the fortuitous occurrence of nuclease recognition sites at interior locations in the target polynucleotide. Blocking can be achieved in a variety of ways, including methylation and treatment by sequence-specific aptamers, DNA binding proteins, or oligonucleotides that form triplexes. Whenever natural protein endonucleases are employed, recognition sites can be conveniently blocked by methylating the target polynucleotide with the cognate methylase of the nuclease being used. That is, for most if not all type II bacterial restriction endonucleases, there exists a so-called "cognate" methylases that methylates its recognition site. Many such methylases are disclosed in Robers et al (cited above) and Nelson et al. Nucleic Acids Research, 21: 3139–3154 (1993). and are commercially available from a variety of sources, particularly New England Biolabs (Beverly, Mass.). Alternatively, if a PCR step is employed in preparing target polynucleotides for sequencing, 5-methylcytosine triphosphates may be used during amplification so that the natural cytosine are replaced by methylated cytosines in the amplicon. This later approach has the added advantage of eliminating the need to treat a target polynucfeotide bound to a solid phase support with another enzyme.

The method of the invention may include one or more capping steps in each cycle. The term "capping" is used herein by analogy with the usage of the term in polynucleotide synthesis, e.g. Andrus et al, U.S. Pat. No. 4,816,571. It refers to a treatment of target polynucleotides that have failed to undergo, or participate in, a transformation of a prior step. The capping treatment is designed to render a target polynucleotide inert to participation in any treatment steps of subsequent cycles. In this manner spurious signals from "out of phase" cleavages or ligations are prevented. Capping steps may be implemented after ligation steps and/or cleavage steps. For example, a first capping step may be iimplemented after unligated adaptor is washed from the target polynucleotide. If the nuclease being employed leaves a 5' protruding strand on the target polynucleotides, capping is preferably accomplished by exposing the unreacted target polynucleotides to a mixture of the four dideoxynucleoside triphosphates, or other chain-terminating nucleoside triphosphates, and a DNA polymerase. The DNA polymerase extends the 3' strand of the unreacted target polynucleotide by one chain-terminating nucleotide, e.g. a dideoxynucleotide, thereby rendering it incapable of ligating in subsequent cycles.

A second capping step may be implemented after the cleavage step. Depending on the recognition site of the type IIs nuclease employed, adaptors that fail to cleave may be "capped" by treatment with a methylase to block the type IIs recognition site in the adaptor, thereby rendering the ligated complex inert to further processing steps. Adaptors may also be constructed that include an additional restriction site that permits capping by cleavage of adaptors that fail to cleave under treatment by the type IIs nuclease. An example of such a adaptor is shown below (SEQ ID NO: 3):

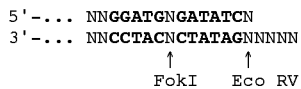

```
5'-... NNGGATGNGATATCN
3'-... NNCCTACNCTATAGNNNNN
              ↑        ↑
            FokI    Eco RV
```

Treatment with Eco RV results in the formation of a blunt ended target polynucleotide that will be incapable of participating in subsequent ligations (in embodiments requiring protruding ends). Such capping approaches have the added advantage of removing any labels that may be attached to the terminus of the ligated adaptor, thereby reducing a contribution to noise in subsequent detection steps.

Clearly, one of ordinary skill in the art could combine features of the embodiments set forth above to design still further embodiments in accordance with the invention, but not expressly set forth above.

Solid Phase Supports

Solid phase supports for use with the invention may have a wide variety of forms, including microparticles, beads, and membranes, slides, plates, micromachined chips, and the like. Likewise, solid phase supports of the invention may comprise a wide variety of compositions, including glass, plastic, silicon, alkanethiolate-derivatized gold, cellulose, low cross-linked and high cross-linked polystyrene, silica gel, polyamide, and the like. Preferably, either a population of discrete particles are employed such that each has a uniform coating, or population, of substantially identical polynucleotides, or a single or a few supports are employed with spatially discrete regions each containing a uniform coating, or population, of substantially identical polynucleotides. In the latter embodiment, the area of the regions may vary according to particular applications; usually, the regions range in area from several $\mu m^2$, e.g. 3–5, to several hundred $\mu m^2$, e.g. 100–500. Preferably, such regions are spatially discrete so that signals generated by events. e.g. fluorescent emissions, at adjacent regions can be resolved by the detection system being employed.

Preferably, the solid phase supports employed with the invention are microparticles, including microparticles made of controlled pore glass (CPG), highly cross-linked polystyrene, acrylic copolymers, cellulose, nylon, dextran, latex, polyacrolein, and the like, which are disclosed in the following exemplary references: Meth. Enzymol. Section A, pages 11–147, vol. 44 (Academic Press, New York, 1976); U.S. Pat. Nos. 4,678,814; 4,413,070; and 4,046;720; and Pon, Chapter 19, in Agrawal, editor, Methods in Molecular Biology, Vol. 20, (Humana Press, Totowa, N.J., 1993). Microparticle supports further include commercially available CPG and polystyTene beads (e.g. available from Applied Biosystems, Foster City, Calif.); derivatized magnetic beads, polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on the conditions under which the bead-polynucleotide conjugates are used. For example, in applications involving successive processing with enzymes, supports and linkers that minimize steric hindrance of the enzymes and that facilitate access to substrate are preferred. Other important factors to be considered in selecting the most appropriate microparticle support include size uniformity, efficiency as a synthesis support, degree to which surface area known, and optical properties, e.g. clear smooth beads provide instrumentational advantages when handling large numbers of beads on a surface. Generally, the size and shape of a microparticle is not critical; however, microparticles in the size range of a few, e.g. 1–2, to several hundred, e.g. 200–1000 $\mu m$ diameter are preferable.

In other preferred applications, non-porous microparticles are employed for their optical properties, which may be advantageously used when tracking large numbers of microparticles on planar supports, such as a microscope slide. Particularly preferred non-porous microparticles are the glycidal methacrylate (GMA) beads available from Bangs Laboratories (Carmel, Ind.). Such microparticles are useful in a variety of sizes and derivatized with a variety of linkage groups for synthesizing tags or tag complements. Preferably, for massively parallel manipulations of tagged microparticles, 5 $\mu m$ diameter GMA beads are employed.

EXPERIMENTAL

Sequencing a Target Polynucleotide Amplified from pGEM7Z: Identification of Nucleotides by the Ligation Reaction In this example, a segment of plasmid pGEM7Z (Promega, Madison, Wis.) is amplified and attached to glass beads via a double stranded DNA linker, one strand of which is synthesized directly onto (and therefore covalently linked to) the beads. In each sequencing cycle after ligation, an aliquot of beads are removed from the reaction mixture and loaded onto a gel electrophoresis column for analyzing the non-covalently bound strand of the ligated complex. The probes are designed so that the non-covalently bound strand would always carry a fluorescent label for analysis.

A 47-mer oligonucleotide is synthesized directly on KF169 Ballotini beads using a standard automated DNA synthesizer protocol. The complementary strand to the 47-mer is synthesized separately and purified by HPLC. When hybridized the resulting duplex has a Bst XI restriction site at the end distal from the bead. The complementary strand is hybridized to the attached 47-mer in the following mixture: 25 $\mu l$ complementary strand at 200 pmou/$\mu l$; 20 mg KF169 Ballotini beads with the 47-mer; 6 $\mu l$ New England Biolabs #3 restriction buffer; and 25 $\mu l$ distilled water. The mixture is heated to 93° C. and then slowly cooled to 55° C., after which 40 units of Bst XI (at 10 units/$\mu l$) is added to bring the reaction volume to 60 $\mu l$. The mixture is incubated at 55° C. for 2 hours after which the beads are washed three times in TE (pH 8.0).

The segment of pGEM7Z to be attached to the beads is prepared as follows: Two PCR primers were prepared using standard protocols (SEQ ID NO: 4 and SEQ ID NO: 5):

```
Primer   5'-CTAAACCATTGGTATGGGCCAGTGAATTGTAATA
1:

Primer   5'-CGCGCAGCCCGCATCGTTTATGCTACAGACTGTC-
2:
                         AGTGCAGCTCTCCGATCCAAA
```

The PCR reaction mixture consists of the following: 1 $\mu l$ pGEM7Z at 1 ng/$\mu l$; 10 $\mu l$ primer 1 at 10 pmol/$\mu l$; 10 $\mu l$ primer 2 at 10 pmol/μl; 10 μl deoxyribonucleotide triphosphates at 2.5 mM; 10 μl 10×PCR buffer (Perkin-Elmer); 0.5 μl Taq DNA polymerase at 5 units/μl; and 58 μl distilled water to give a final volume of 100 μl. The reaction mixture was subjected to 25 cycles of 93° C. for 30 sec; 60° C. for 15 sec; and 72° C. for 60 sec, to give a 172 basepair product, which is successively digested with Bbv I (100 μl PCR reaction mixture, 12 μl 10×#1 New England Biolabs buffer, 8 μl Bbv I at 1 unit/μl incubate at 37° C. for 6 hours) and with Bst XI (to the Bbv I reaction mixture is added: 5 μl 1 M NaCl, 67 μl distilled water, and 8 μl Bst XI at 10 units/μl, and the resulting mixture is incubated at 55° C. for 2 hours).

After passing the above reaction mixture through a Centricon 30 (Amicon, Inc.) spin column following manufacturer's protocol, the Bbv I/Bst XI-restricted fragment is ligated to the double stranded linker attached to the Ballotini beads in the following mixture: 17 μl Bbv I/Bst XI-restricted fragment (10 μg), 10 μl beads (20 mg), 6 ml 10× ligation buffer (New England Biolabs, referred to below as NEB), 5 μl T4 DNA ligase at 2000 units/μl, and 22 μl distilled water, which mixture is incubated at 25° C. for 4 hours, after which the beads are washed 3 times with TE (pH 8.0), leaving the following target polynucleotide for sequencing having a 5' phosphate:

```
                    . . . TCTGTAGCT
[BEAD]--            . . . AGACATCGAATTTp-5'
```

The 5' phosphate is removed by treating the bead mixture with an alkaline phosphatase, e.g. from calf intestine, available from New England Biolabs (Beverly, Mass.), using manufacturer's protocol.

The strands of the following adaptors (24 nucleotides in labeled strand and 18 nucleotides in non-labeled strand) are separately synthesized on an automated DNA synthesizer (model 392 Applied Biosystems, Foster City) using standard methods (SEQ ID NO: 6, SEQ ID NO: 7, SEQ ID NO: 8, and SEQ ID NO: 9):

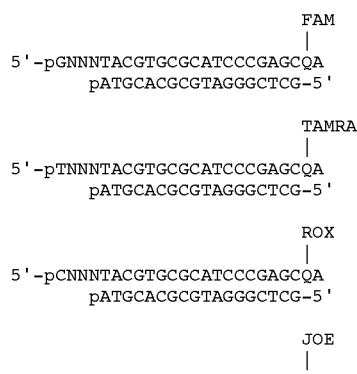

```
                         FAM
                          |
        5'-pGNNNTACGTGCGCATCCCGAGCQA
              pATGCACGCGTAGGGCTCG-5'

TAMRA
                          |
        5'-pTNNNTACGTGCGCATCCCGAGCQA
              pATGCACGCGTAGGGCTCG-5'

ROX
                          |
        5'-pCNNNTACGTGCGCATCCCGAGCQA
              pATGCACGCGTAGGGCTCG-5'

JOE
                          |
```

-continued
```
        5'-pANNNTACGTGCGCATCCCGAGCQA
              pATGCACGCGTAGGGCTCG-5'
``` where p is a monophosphate, N indicates A, C, G, or T, Q is a branched linker carrying a protected amino group for attachment of a label (e.g. Uni-Link AminoModifier, available from Clontech Laboratories, Palo Alto, Calif.). TAMRA (tetramethylrhodamine), FAM (fluorescein), ROX (rhodamine X), and JOE (2',7'-dimethoxy-4',5'-dichlorofluorescein) are available from Perkin-Elmer Applied Biosystems Division (Foster City, Calif.). Equal molar quantities of each adaptor are combined in TE to form a mixture at a concentration of 1000 pmol/μl.

Ligation of the adaptors to the target polynucleotide is carried out in a mixture consisting of 5 μl beads (20 mg), 3 μl NEB 10× ligase buffer, 5 μl adaptor mix, 2.5 μl NEB T4 DNA ligase (2000 units/μl), and 14.5 μl distilled water. The mixture is incubated at 16° C. for 30 minutes, after which the beads are washed 3 times in TE (pH 8.0).

After centrifugation and removal of TE. the 3' phosphates of the ligated adaptors are removed by treating the polynucleotide-bead mixture with calf intestinal alkaline phosphatase (CIP) (New England Biolabs, Beverly, Mass.), using the manufacturer's protocol. After removal of the 3' phosphates, the CIP is inactivated by proteolytic digestion, e.g. using Pronase™ (available form Boeringer Mannhiem, Indianapolis, Ind.), or an equivalent protease, with the manufacturer's protocol. The polynucleotide-bead mixture is then washed, treated with T4 polynucleotide kinase (New England Biolabs, Beverly, Mass.) to add a 5' phosphate at the gap between the target polynucleotide and the adaptor. After washing, the bead-polynucleotide mixture is treated with T4 DNA ligase, as described above, to complete the ligation of the adaptors to the target polynucleotide.

Cleavages are carried out in a mixture consisting of 5 μl beads (20 mg), 3 μl 10× NEB buffer #3, 3 μl NEB Fok I(4 units/μl), and 19 μl distilled water. The mixture is incubated at 37° C. for 30 minutes, after which the beads are washed 3 times in TE (pH 8.0).

After each ligation, a sample of the beads with the ligated complex is removed for size analysis on a model 373 DNA sequencer using 672 GeneScan software (Applied Biosystems). The readout of the system provides a different colored curve for fragments labeled with the four different dyes (black for TAMRA, blue for FAM, green for JOE, and red for ROX). A 6% denaturing (8 M urea) polyacrylamide gel is employed in accordance with manufacturer's protocols. About 0.5 mg of beads are placed in 4 μl of formamide loading buffer in accordance with the manufacturer's protocol for analyzing sequencing fragments. Samples are heated to 95° C. for 2 min then cooled by placing on ice, after which the entire sample is loaded into one lane for analysis.

We claim:

1. A double stranded nucleic acid adaptor having a 3' blocked protuding strand, of the formula:

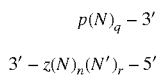

where

N and N' are complementary nucleotides, p is a phosphate group, z is a 3' blocking group, n is an integer between 2 and 5, inclusive, q is an integer greater than or equal to 8, r is an integer greater than or equal to 8 which may be the same or different from q, and the 3' blocked protruding strand is 2 to 6 nucleotides long.

2. The adaptor of claim 1 wherein z is a phosphate group, q is in the range of between 12 and 50, and r is in the range of between 12 and 50.

3. The adaptor of claim 1, where the 3' blocked protruding strand is 4 nucleotides long.

4. A double stranded nucleic acid adaptor having a 5' phosphorylated protruding strand, of the formula:

$5' - p(N)_n(N)_q - 3'$

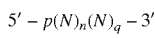

where

N and N' are complementary nucleotides, p is a phosphate group, z is a 3' blocking group, n is an integer between 2 and 5, inclusive, q is an integer greater than or equal to 8, r is an integer greater than or equal to 8 which may be the same or different frog q, and the 5' protruding strand is from 2 to 6 nucleotides long.

5. A composition of matter comprising a microparticle having a uniform population of substantially identical double stranded polynucleotides attached, each polynucleotide of the uniform population having a 5'-dephosphorylated protruding strand at an end distal to the microparticle.

6. The composition of claim 5 wherein said protruding strand is between 2 and 5 nucleotides in length.

7. The composition of claim 6 wherein said uniform population of substantially identical polynucleotides is a population of substantially identical cDNAs.

8. The composition of claim 7 wherein said microparticle is selected from the group consisting of CPG microparticles, GMA microparticles, and polystyrene microparticles.

* * * * *